(12) United States Patent
Scalzo et al.

(10) Patent No.: US 8,156,718 B2
(45) Date of Patent: *Apr. 17, 2012

(54) METHOD OF PREPARING A PACKAGED ANTIMICROBIAL MEDICAL DEVICE

(75) Inventors: Howard Scalzo, Kenilworth, NJ (US); Jerome A. Fischer, Warren, NJ (US); Stephen Rothenburger, Neshanic Station, NJ (US); Robert Cerwin, Pipersville, PA (US); James R. McDivitt, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/417,518

(22) Filed: Apr. 2, 2009

(65) Prior Publication Data

US 2009/0301033 A1 Dec. 10, 2009

Related U.S. Application Data

(63) Continuation of application No. 11/301,365, filed on Dec. 13, 2005, now Pat. No. 7,513,093.

(51) Int. Cl.
B65B 55/02 (2006.01)
(52) U.S. Cl. ............ 53/425; 53/449; 206/63.3; 606/228
(58) Field of Classification Search ............... 53/425, 53/426, 449, 167; 606/228, 229, 230, 232; 604/172; 206/63.3
See application file for complete search history.

(56) References Cited

U.S. PATENT DOCUMENTS

| 809,725 A | 1/1906 | Neff |
| 2,917,878 A | 12/1958 | Edwin et al. |
| 2,947,282 A | 8/1960 | Brown |
| 3,202,273 A | 8/1965 | Riall |
| 3,613,879 A | 10/1971 | Kemble |
| 3,629,477 A | 12/1971 | Model et al. |

(Continued)

FOREIGN PATENT DOCUMENTS

AU 52834/86 B 5/1987

(Continued)

OTHER PUBLICATIONS

Database EMBASE on STN, AN 2003062. Barbolt T.A. "Chemistry and Safety of Triclosan, and Its Use as an Antimicrobial Coating on Coated VICRYL. Plus Antibacterial Suture (Coated Polyglactin 910 Suture with Triclosan)". Surgical Infections, May 2002, vol. 3, No. 3, Suplement 1, pp. S-45-S-53, see abstract.

(Continued)

*Primary Examiner* — Christopher Harmon
(74) *Attorney, Agent, or Firm* — Roberts Mlotkowski Safran & Cole, P.C.

(57) ABSTRACT

A method of making a packaged antimicrobial suture comprising the steps of providing a containment compartment that is substantially free of an antimicrobial agent; positioning a suture within the containment compartment, said suture comprising one or more surfaces having an antimicrobial agent disposed thereon, said antimicrobial agent being selected from the group consisting of halogenated hydroxyl ethers, acyloxydiphenyl ethers, and combinations thereof; placing the containment compartment having the suture in an outer package; and subjecting the outer package, the containment compartment and the suture to time, temperature and pressure conditions sufficient to vapor transfer an effective amount of the antimicrobial agent from the suture to the containment compartment, while retaining an effective amount of said antimicrobial agent on the suture, thereby substantially inhibiting bacterial colonization on the suture and the containment compartment.

9 Claims, 5 Drawing Sheets

U.S. PATENT DOCUMENTS

| | | |
|---|---|---|
| 3,642,003 A | 2/1972 | Kurtz |
| 3,726,057 A | 4/1973 | Kemble |
| 3,815,315 A | 6/1974 | Glick |
| 3,862,304 A | 1/1975 | Kurtz |
| 3,896,812 A * | 7/1975 | Kurtz .......................... 606/228 |
| 3,939,971 A | 2/1976 | Tulis |
| 3,991,766 A | 11/1976 | Schmitt et al. |
| 4,024,871 A | 5/1977 | Stephenson |
| 4,105,034 A | 8/1978 | Shalaby et al. |
| 4,230,663 A | 10/1980 | Forstrom et al. |
| 4,476,590 A | 10/1984 | Scales et al. |
| 4,482,053 A | 11/1984 | Alpern et al. |
| 4,603,538 A | 8/1986 | Shave |
| 4,605,564 A | 8/1986 | Kulla et al. |
| 4,615,705 A | 10/1986 | Scales et al. |
| 4,728,323 A | 3/1988 | Matson |
| 4,846,844 A | 7/1989 | De Leon et al. |
| 4,853,978 A | 8/1989 | Stockum |
| 4,856,504 A | 8/1989 | Yamamoto et al. |
| 4,946,043 A | 8/1990 | Roshdy et al. |
| 4,952,419 A | 8/1990 | De Leon et al. |
| 5,019,096 A | 5/1991 | Fox et al. |
| 5,037,429 A | 8/1991 | Hermes et al. |
| 5,052,551 A | 10/1991 | Cerwin et al. |
| 5,066,328 A | 11/1991 | Zlotnik |
| 5,091,442 A | 2/1992 | Milner |
| 5,154,283 A * | 10/1992 | Brown .......................... 206/63.3 |
| 5,165,913 A | 11/1992 | Hill et al. |
| 5,180,605 A | 1/1993 | Milner |
| 5,261,421 A | 11/1993 | Milner |
| 5,284,240 A | 2/1994 | Alpern et al. |
| 5,295,979 A | 3/1994 | DeLaurentis et al. |
| 5,359,831 A | 11/1994 | Brown et al. |
| 5,468,252 A * | 11/1995 | Kaplan et al. ................. 606/228 |
| 5,468,562 A | 11/1995 | Farivar et al. |
| 5,474,797 A | 12/1995 | Sioshansi et al. |
| 5,518,730 A | 5/1996 | Fuisz |
| 5,529,175 A | 6/1996 | Brunken |
| 5,534,288 A | 7/1996 | Gruskin et al. |
| 5,556,699 A | 9/1996 | Niira et al. |
| 5,562,211 A | 10/1996 | Simons et al. |
| 5,607,681 A | 3/1997 | Galley et al. |
| 5,708,023 A | 1/1998 | Modak et al. |
| 5,722,992 A | 3/1998 | Goldmann |
| 5,756,145 A | 5/1998 | Darouiche |
| 5,772,640 A | 6/1998 | Modak et al. |
| 5,804,628 A | 9/1998 | Busnel et al. |
| 5,853,745 A | 12/1998 | Darouiche |
| 5,868,244 A | 2/1999 | Ivanov et al. |
| 5,889,075 A | 3/1999 | Roby et al. |
| 5,902,283 A | 5/1999 | Darouiche et al. |
| 5,906,273 A | 5/1999 | Pohle et al. |
| 5,906,825 A | 5/1999 | Seabrook, Jr. et al. |
| 5,945,153 A | 8/1999 | Dearnaley |
| 5,965,610 A | 10/1999 | Modak et al. |
| 5,968,207 A | 10/1999 | Li |
| 5,985,934 A | 11/1999 | Gaffney et al. |
| 5,997,815 A | 12/1999 | Anders et al. |
| 6,034,010 A | 3/2000 | Cartwright et al. |
| 6,037,386 A | 3/2000 | Modak et al. |
| 6,047,815 A | 4/2000 | Cerwin et al. |
| 6,083,208 A | 7/2000 | Modak et al. |
| 6,087,415 A | 7/2000 | Vanderlaan et al. |
| 6,093,414 A | 7/2000 | Capelli |
| 6,106,505 A | 8/2000 | Modak et al. |
| 6,165,920 A | 12/2000 | Rubin et al. |
| 6,224,579 B1 | 5/2001 | Modak et al. |
| 6,238,686 B1 | 5/2001 | Burrell et al. |
| 6,260,699 B1 | 7/2001 | Kaplan et al. |
| 6,315,788 B1 | 11/2001 | Roby |
| 6,481,568 B1 * | 11/2002 | Cerwin et al. ................. 206/63.3 |
| 6,494,898 B1 | 12/2002 | Roby et al. |
| 6,495,100 B1 | 12/2002 | Lin et al. |
| 6,706,024 B2 | 3/2004 | Modak et al. |
| 6,837,027 B2 | 1/2005 | Hickey |
| 6,916,480 B2 | 7/2005 | Anderson et al. |
| 7,275,640 B2 | 10/2007 | Bourne et al. |
| 7,513,093 B2 * | 4/2009 | Scalzo et al. ..................... 53/425 |
| 7,651,661 B2 | 1/2010 | Raad et al. |
| 2001/0010016 A1 | 7/2001 | Modak et al. |
| 2001/0016589 A1 | 8/2001 | Modak et al. |
| 2001/0024661 A1 | 9/2001 | Modak et al. |
| 2002/0055759 A1 | 5/2002 | Shibuya |
| 2003/0108761 A1 | 6/2003 | Eddlemon |
| 2003/0138347 A1 | 7/2003 | Lin |
| 2004/0220614 A1 | 11/2004 | Scalzo et al. |
| 2006/0231443 A1 | 10/2006 | Jonasson et al. |
| 2008/0171972 A1 | 7/2008 | Stopek |
| 2009/0301033 A1 | 12/2009 | Scalzo et al. |
| 2010/0036359 A1 | 2/2010 | Stopek et al. |
| 2010/0078336 A1 | 4/2010 | Reyhan et al. |
| 2010/0116694 A1 | 5/2010 | Stopek et al. |

FOREIGN PATENT DOCUMENTS

| | | |
|---|---|---|
| CA | 2185056 | 3/1997 |
| CN | 2115083 U | 9/1992 |
| CN | 2190968 Y | 3/1995 |
| CN | 1125622 A | 7/1996 |
| EP | 0470443 A2 | 2/1992 |
| EP | 0471441 A1 | 2/1992 |
| EP | 0761243 A1 | 3/1997 |
| EP | 1159972 A2 | 12/2001 |
| GB | 809725 | 3/1959 |
| JP | 49-111794 | 10/1974 |
| JP | 8-164190 A | 6/1996 |
| JP | 10-504756 | 5/1998 |
| JP | 11-500330 | 1/1999 |
| JP | 2000-237289 | 5/2000 |
| TW | 408011 B | 10/2000 |
| TW | 446822 B | 7/2001 |
| WO | 98/09667 | 3/1998 |
| WO | 00/44414 | 8/2000 |
| WO | 01/28601 | 4/2001 |
| WO | 2008/045338 A2 | 4/2008 |

OTHER PUBLICATIONS

Database ACS on STN, AN 133: 366471. Anuzis et al. "Acetate antimicrobial threads". LT 4568 B, Oct. 25, 1999, abstract.

Josephine J. Braid et al., "The antibacterial activity of triclosan-impregnated storage boxes against *Staphylococcus aureus, Escherichia coli, Pseudomonas aeruginosa, Bacillus cereus* and *Shewanella putrefaciens* in conditions simulating domestic use" Journal of Antimocrobial Chemotherapy (2002) vol. 49 pp. 87-94.

\* cited by examiner

METHOD OF PREPARING A PACKAGED ANTIMICROBIAL MEDICAL DEVICE

CROSS-REFERENCE TO PRIOR APPLICATIONS

This application is a continuation of U.S. Ser. No. 11/301,365, filed on Dec. 13, 2005, which is a continuation-in-part of U.S. Ser. No. 10/808,669, filed on Mar. 25, 2004, which is a continuation-in-part of U.S. Ser. No. 10/603,317 filed on Jun. 25, 2003, which is a continuation-in-part of U.S. Ser. No. 10/367,497 filed on Feb. 15, 2003, which claimed the benefit of U.S. Provisional Application No. 60/416,114 filed on Oct. 4, 2002, the contents of each are hereby incorporated by reference in their entirety.

FIELD OF THE INVENTION

The present invention relates to a packaged antimicrobial medical device and its methods of making.

BACKGROUND OF THE INVENTION

Each year, patients undergo a vast number of surgical procedures in the United States. Current data shows about twenty-seven million procedures are performed per year. Post-operative or surgical site infections ("SSIs") occur in approximately two to three percent of all cases. This amounts to more than 675,000 SSIs each year.

The occurrence of SSIs is often associated with bacteria that can colonize on implantable medical devices used in surgery. During a surgical procedure, bacteria from the surrounding atmosphere may enter the surgical site and attach to the medical device. Specifically, bacteria can spread by using the implanted medical device as a pathway to surrounding tissue. Such bacterial colonization on the medical device may lead to infection and trauma to the patient. Accordingly, SSIs may significantly increase the cost of treatment to patients.

Implantable medical devices that contain antimicrobial agents applied to or incorporated within have been disclosed and/or exemplified in the art. Examples of such devices are disclosed in European Patent Application No. EP 0 761 243. Actual devices exemplified in the application include French Percuflex catheters. The catheters were dip-coated in a coating bath containing 2,4,4'-tricloro-2-hydroxydiphenyl ether (Ciba Geigy Irgasan (DP300)) and other additives. The catheters then were sterilized with ethylene oxide and stored for thirty days. Catheters coated with such solutions exhibited antimicrobial properties, i.e., they produced a zone of inhibition when placed in a growth medium and challenged with microorganism, for thirty days after being coated. It is not apparent from the application at what temperature the sterilized, coated catheters were stored.

Most implantable medical devices are manufactured, sterilized and contained in packages until opened for use in a surgical procedure. During surgery, the opened package containing the medical device, packaging components contained therein, and the medical device, are exposed to the operating room atmosphere, where bacteria from the air may be introduced. Incorporating antimicrobial properties into the package and/or the packaging components contained therein substantially prevents bacterial colonization on the package and components once the package has been opened. The antimicrobial package and/or packaging components in combination with the incorporation of antimicrobial properties onto the medical device itself would substantially ensure an antimicrobial environment about the sterilized medical device.

SUMMARY OF THE INVENTION

The present invention relates to packaged antimicrobial medical devices and methods for preparing such packaged medical devices. In accordance with embodiments of the present invention, an antimicrobial agent is disposed on the surfaces of the medical device. The medical device is positioned within a package or within a packaging component such as a containment compartment within a package, and upon being subjected to sufficient conditions, a portion of the antimicrobial agent transfers from the medical device to the package and/or the containment compartment. The transfer of the antimicrobial agent is in an amount sufficient to inhibit bacterial growth on and about the medical device, the package and/or the containment compartment.

An embodiment of the packaged antimicrobial medical device includes at least one package having an inner surface with an antimicrobial agent disposed thereon, the antimicrobial agent being selected from halogenated hydroxyl ethers, acyloxydiphenyl ethers, and combinations thereof, in an amount sufficient to substantially inhibit bacterial colonization on the package; and at least one medical device positioned within the package, the medical device having one or more surfaces having an antimicrobial agent disposed thereon, the antimicrobial agent being selected from halogenated hydroxyl ethers, acyloxydiphenyl ethers, and combinations thereof, in an amount sufficient to substantially inhibit bacterial colonization on the medical device.

Another embodiment of the packaged antimicrobial medical device includes a package having an inner surface and a containment compartment for securing the medical device and that resides within the package. In this embodiment, at least one surface of the containment compartment includes an antimicrobial agent disposed thereon, present in an amount sufficient to substantially inhibit bacterial colonization on the containment compartment. In an alternate embodiment, the inner surface of the package and at least one surface of the containment compartment include an antimicrobial agent disposed thereon, present in an amount sufficient to substantially inhibit bacterial colonization on the package and the containment compartment. The packaged medical device also includes at least one medical device positioned within the containment compartment. The medical device also has one or more surfaces having an antimicrobial agent disposed thereon. The antimicrobial agent is present on the medical device in an amount sufficient to substantially inhibit bacterial colonization on the medical device. The antimicrobial agent disposed on the package, the containment compartment and medical device may be selected from antimicrobial compounds which include halogenated hydroxyl ethers, acyloxydiphenyl ethers, and combinations thereof.

Another embodiment is an antimicrobial suture assembly comprising a containment compartment comprising one or more surfaces having an antimicrobial agent disposed thereon, the antimicrobial agent being selected from the group consisting of halogenated hydroxyl ethers, acyloxydiphenyl ethers, and combinations thereof, in an amount sufficient to substantially inhibit bacterial colonization on the containment compartment; and a suture positioned within the containment compartment, the suture comprising one or more surfaces having an antimicrobial agent disposed thereon, the antimicrobial agent being selected from the group consisting of halogenated hydroxyl ethers, acyloxydiphenyl ethers, and combinations thereof, in an amount sufficient to substantially inhibit bacterial colonization on the suture.

The present invention is also directed to a method for preparing a packaged antimicrobial medical device, which includes the steps of providing a package and/or a containment compartment that is substantially free of an antimicrobial agent; positioning a medical device within the package or the containment compartment, the medical device including one or more surfaces having an antimicrobial agent disposed thereon, the antimicrobial agent being selected from the group consisting of halogenated hydroxyl ethers, acyloxydiphenyl ethers, and combinations thereof; subjecting the package and/or the containment compartment and the medical device to conditions sufficient to transfer a first portion of the antimicrobial agent from the medical device to the package and/or the containment compartment, while retaining a second portion of the antimicrobial agent on the surface of the medical device, thereby substantially inhibiting bacterial colonization on the medical device, the package and/or the containment compartment.

DETAILED DESCRIPTION OF EMBODIMENTS OF THE INVENTION

Packaged Antimicrobial Medical Device

Figure 1:
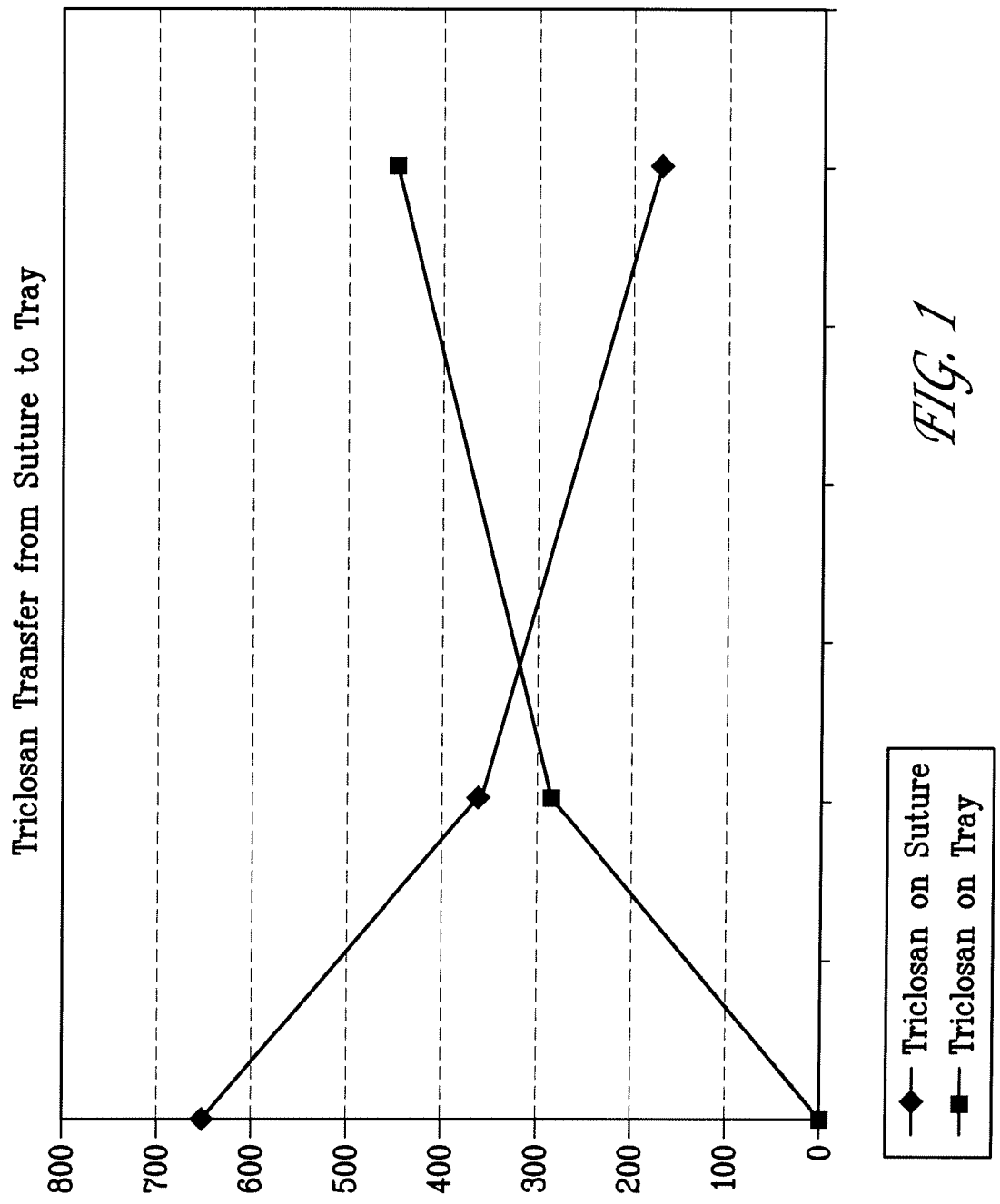
FIG. 1 is a graph illustrating the transfer of an antimicrobial agent from the medical device to a containment compartment at 55 C as a function of time.

One embodiment of the packaged antimicrobial medical device includes at least one package having an inner surface. The inner surface includes an antimicrobial agent disposed thereon, present in an amount sufficient to substantially inhibit bacterial colonization on the package. The packaged medical device also includes at least one medical device positioned within the package. The medical device also has one or more surfaces having an antimicrobial agent disposed thereon. The antimicrobial agent is present on the medical device, in an amount sufficient to substantially inhibit bacterial colonization on the medical device. The antimicrobial agent disposed on the package and medical device may be selected from antimicrobial compounds which include halogenated hydroxyl ethers, acyloxydiphenyl ethers, and combinations thereof.

In another embodiment, the packaged medical device includes a package having an inner surface and a containment compartment for securing the medical device and that resides within the package. In this embodiment, at least one surface of the containment compartment includes an antimicrobial agent disposed thereon, present in an amount sufficient to substantially inhibit bacterial colonization on the containment compartment. In an alternate embodiment, the inner surface of the package and at least one surface of the containment compartment include an antimicrobial agent disposed thereon, present in an amount sufficient to substantially inhibit bacterial colonization on the package and the containment compartment. The packaged medical device also includes at least one medical device positioned within the containment compartment. The medical device also has one or more surfaces having an antimicrobial agent disposed thereon. The antimicrobial agent is present on the medical device, in an amount sufficient to substantially inhibit bacterial colonization on the medical device. The antimicrobial agent disposed on the package, the containment compartment and medical device may be selected from antimicrobial compounds which include halogenated hydroxyl ethers, acyloxydiphenyl ethers, and combinations thereof.

Another embodiment is an antimicrobial suture assembly comprising a containment compartment comprising one or more surfaces having an antimicrobial agent disposed thereon, the antimicrobial agent being selected from the group consisting of halogenated hydroxyl ethers, acyloxydiphenyl ethers, and combinations thereof, in an amount sufficient to substantially inhibit bacterial colonization on the containment compartment; and a suture positioned within the containment compartment, the suture comprising one or more surfaces having an antimicrobial agent disposed thereon, the antimicrobial agent being selected from the group consisting of halogenated hydroxyl ethers, acyloxydiphenyl ethers, and combinations thereof, in an amount sufficient to substantially inhibit bacterial colonization on the suture.

The medical devices described herein are generally implantable medical devices, including but not limited to mono and multifilament sutures, surgical meshes such as hernia repair mesh, hernia plugs, brachy seed spacers, suture clips, suture anchors, adhesion prevention meshes and films, and suture knot clips. Also included are implantable medical devices that are absorbable and non-absorbable. An absorbable polymer is defined as a polymer that, when exposed to physiological conditions, will degrade and be absorbed by the body over a period of time. Absorbable medical devices typically are formed from generally known, conventional absorbable polymers including, but not limited to, glycolide, lactide, co-polymers of glycolide, or mixtures of polymers, such as polydioxanone, polycaprolactone and equivalents thereof. Preferably, the polymers include polymeric materials selected from the group consisting of greater than about 70% polymerized glycolide, greater than about 70% polymerized lactide, polymerized 1,4-dioxan-2-one, greater than about 70% polypeptide, copolymers of glycolide and lactide, greater than about 70% cellulosics and cellulosic derivatives. Examples of absorbable medical device include mono and multifilament sutures. The multifilament suture includes sutures wherein a plurality of filaments are formed into a braided structure. Examples of non-absorbable medical devices include mono and multifilament sutures, surgical meshes such as hernia repair mesh, hernia plugs and brachy seed spacers, which may be polymeric or nonpolymeric.

Suitable antimicrobial agents may be selected from, but are not limited to, halogenated hydroxyl ethers, acyloxydiphenyl ethers, or combinations thereof. In particular, the antimicrobial agent may be a halogenated 2-hydroxy diphenyl ether and/or a halogenated 2-acyloxy diphenyl ether, as described in U.S. Pat. No. 3,629,477, and represented by the following formula:

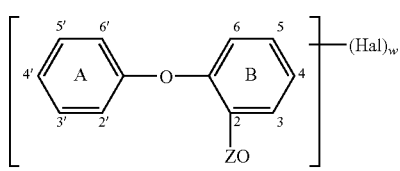

In the above formula, each Hal represents identical or different halogen atoms, Z represents hydrogen or an acyl group, and w represents a positive whole number ranging from 1 to 5, and each of the benzene rings, but preferably ring A can also contain one or several lower alkyl groups which may be halogenated, a lower alkoxy group, the allyl group, the cyano group, the amino group, or lower alkanoyl group. Preferably, methyl or methoxy groups are among the useful lower alkyl and lower alkoxy groups, respectively, as substituents in the benzene rings. A halogenated lower alkyl group, trifluoromethyl group is preferred.

Antimicrobial activity similar to that of the halogen-o-hydroxy-diphenyl ethers of the above formula is also attained using the O-acyl derivatives thereof which partially or completely hydrolyze under the conditions for use in practice. The esters of acetic acid, chloroacetic acid, methyl or dimethyl carbamic acid, benzoic acid, chlorobenzoic acid, methylsulfonic acid and chloromethylsulfonic acid are particularly suitable.

One particularly preferred antimicrobial agent within the scope of the above formula is 2,4,4'-trichloro-2'-hydroxy-diphenyl ether, commonly referred to as triclosan (manufactured by Ciba Geigy under the trade name Irgasan DP300 or Irgacare MP). Triclosan is a broad-spectrum antimicrobial agent that has been used in a variety of products, and is effective against a number of organisms commonly associated with SSIs. Such microorganisms include, but are not limited to, genus *Staphylococcus, Staphylococcus epidermidis, Staphylococcus aureus*, methicillin-resistant *Staphylococcus epidermidis*, methicillin-resistant *Staphylococcus aureus*, and combinations thereof.

In addition to the antimicrobial agents described above, the medical device optionally may have a biocide, a disinfectant and/or an antiseptic, including but not limited to alcohols such as ethanol and isopropanol; aldehydes such as glutaraldehyde and formaldehyde; anilides such as triclorocarbanilide; biguanides such as chlorhexidine; chlorine-releasing agents such as sodium hypochlorite, chlorine dioxide and acidified sodium chlorite; iodine-releasing agents such as povidone-iodine and poloxamer-iodine; metals such as silver nitrate, silver sulfadiazine, other silver agents, copper-8-quinolate and bismuth thiols; peroxygen compounds such as hydrogen peroxide and peracetic acid; phenols; quaternary ammonium compounds such as benzalkonium chloride, cetrimide and ionenes-polyquaternary ammonium compounds. The medical device optionally may have antibiotics, including but not limited to penicillins such as amoxicillin, oxacillin and piperacillin; cephalosporins parenteral such as cefazolin, cefadroxil, cefoxitin, cefprozil, cefotaxime and cefdinir; monobactams such as aztreonam; beta-lactamase inhibitors such as clavulanic acid sulbactam; glycopeptide such as vancomycin; polymixin; quinolones such as nalidixic acid, ciprofloxacin and levaquin; metranidazole; novobiocin; actinomycin; rifampin; aminoglycosides such as neomycin and gentamicin; tetracyclines such as doxycycline; chloramphenicol; macrolide such as erythromycin; clindamycin; sulfonamide such as sulfadiazine; trimethoprim; topical antibiotics; bacitracin; gramicidin; mupirocin; and/or fusidic acid.

Optionally, the medical device may have antimicrobial peptides such as defensins, magainin and nisin; lytic bacteriophage; surfactants; adhesion blockers such as antibodies, oligosaccharides and glycolipids; oligonucleotides such as antisense RNA; efflux pump inhibitors; photosensitive dyes such as porphyrins; immune modulators such as growth factors, interleukins, interferons and synthetic antigens; and/or chelators such as EDTA, sodium hexametaphosphate, lactoferrin and transferrin.

It is advantageous to use a coating composition as a vehicle for delivering the antimicrobial agent to the surface of the device where such coating already is used conventionally in the manufacture of the device, such as, for example, absorbable and non-absorbable multifilament sutures. Examples of medical devices, as well as coatings that may be applied thereto, may be found in U.S. Pat. Nos. 4,201,216, 4,027,676, 4,105,034, 4,126,221, 4,185,637, 3,839,297, 6,260,699, 5,230,424, 5,555,976, 5,868,244, and 5,972,008, each of which is hereby incorporated herein in its entirety. As disclosed in U.S. Pat. No. 4,201,216, the coating composition may include a film-forming polymer and a substantially water-insoluble salt of a $C_6$ or higher fatty acid. As another example, an absorbable coating composition that may be used for an absorbable medical device may include poly(alkylene oxylates) wherein the alkylene moieties are derived from $C_6$ or mixtures of $C_4$ to $C_{12}$ diols, which is applied to a medical device from a solvent solution, as disclosed in U.S. Pat. No. 4,105,034. The coating compositions of the present invention may include a polymer or co-polymer, which may include lactide and glycolide, as a binding agent. The compositions may also include calcium stearate, as a lubricant, and an antimicrobial agent. Medical devices not conventionally employing a coating in the manufacturing process, however, also may be coated with a composition comprising an antimicrobial agent. The coating may be applied to the device by, for example, dip coating, spray coating, suspended drop coating, or any other conventional coating means.

Absorbable medical devices are moisture sensitive, that is, they are devices that will degrade if exposed to moisture in the atmosphere or in the body. It is known by those of ordinary skill in the art that medical devices made from absorbable polymers may deteriorate and lose their strength if they come into contact with water vapor prior to use during surgery. For instance, the desirable property of in vivo tensile strength retention for sutures will be rapidly lost if the sutures are exposed to moisture for any significant period of time prior to use. Therefore, it is desirable to use a hermetically sealed package for absorbable medical devices. A hermetically sealed package is defined herein to mean a package made of a material that serves as both a sterile barrier and a gas barrier, i.e., prevents or substantially inhibits moisture and gas permeation.

Materials useful for constructing the package for absorbable medical devices, for example, include single and multilayered conventional metal foil products, often referred to as heat-sealable foils. These types of foil products are disclosed in U.S. Pat. No. 3,815,315, which is hereby incorporated by reference in its entirety. Another type of foil product that may be utilized is a foil laminate referred to in the field of art as a peelable foil. Examples of such peelable foil and substrates are disclosed in U.S. Pat. No. 5,623,810, which is hereby incorporated by reference in its entirety. If desired, conventional non-metallic polymer films in addition to or in lieu of metal foil may be used to form the package for absorbable medical devices. Such films are polymeric and may include conventional polyolefins, polyesters, acrylics and the like, combinations thereof and laminates. These polymeric films substantially inhibit moisture and oxygen permeation and may be coated with conventional coatings, such as, for example, mineral coatings that decrease or reduce gas intrusion. The package may comprise a combination of polymer and metal foils, particularly a multi-layer polymer/metal-foil composite.

Nonabsorbable medical devices may be packaged in any of the materials described above. In addition, it is desirable to package nonabsorbable medical devices in a package made of a material that serves as a sterile barrier, such as a porous material, i.e., medical grade paper, or a polymeric film that is permeable to moisture and gas, i.e., TYVEK film, manufactured by DuPont and made from high-density polyethylene fibers.

Packages for surgical needles, sutures and combinations including the suture and a surgical needle typically comprise a suture tray as the containment compartment, for securely holding the suture and/or surgical needle in place. One type of containment compartment typically used for surgical needles and/or sutures is a folder package made from a stiff, medical grade paper. A folder package will typically have a plurality of foldable panels and cut-out tabs and tab pockets. Folder packages for surgical needles and sutures are illustrated and disclosed in the following patents, each of which is hereby incorporated by reference in its entirety: U.S. Pat. Nos. 4,126,221, 4,120,395 and 5,555,976. Another conventionally used containment compartment for surgical needles and/or sutures is a molded plastic tray having a central floor surrounded by an outer winding channel for receiving and retaining a suture, e.g., an oval channel. The containment compartment may further include a medical grade paper or plastic cover that may be mounted to the top of the winding channel, or the molded plastic tray may have molded retainer elements, in order to maintain the suture in the channel. The molded plastic tray may be made from a thermoplastic material selected from the group consisting of polyester, polyvinyl chloride, polypropylene, polystyrene, and polyethylene. Containment compartments having winding channels are illustrated in the following, each of which is hereby incorporated by reference in its entirety: U.S. Pat. Nos. 4,967,902, 5,213,210 and 5,230,424.

Microorganisms of the genus *Staphylococcus* are the most prevalent of all of the organisms associated with device-related surgical site infection. *S. aureus* and *S. epidermidis* are commonly present on patients' skin and as such are introduced easily into wounds. One of the most efficacious antimicrobial agents against *Staphylococcus* is 2,4,4'-trichloro-2'-hydroxydiphenyl ether. This compound has a minimum inhibitory concentration (MIC) against *S. aureus* of 0.01 ppm, as measured in a suitable growth medium and as described by Bhargava, H. et al in the American Journal of Infection Control, June 1996, pages 209-218. The MIC for a particular antimicrobial agent and a particular microorganism is defined as the minimum concentration of that antimicrobial agent that must be present in an otherwise suitable growth medium for that microorganism, in order to render the growth medium unsuitable for that microorganism, i.e., the minimum concentration to inhibit growth of that microorganism. The phrase "an amount sufficient to substantially inhibit bacterial colonization" as used herein is defined as the minimum inhibitory concentration for *S. aureus* or greater.

A demonstration of this MIC is seen in the disk diffusion method of susceptibility. A filter paper disk, or other object, impregnated with a particular antimicrobial agent is applied to an agar medium that is inoculated with the test organism. Where the antimicrobial agent diffuses through the medium, and as long as the concentration of the antimicrobial agent is above the minimum inhibitory concentration (MIC), none of the susceptible organism will grow on or around the disk for some distance. This distance is called a zone of inhibition. Assuming the antimicrobial agent has a diffusion rate in the medium, the presence of a zone of inhibition around a disk impregnated with an antimicrobial agent indicates that the organism is inhibited by the presence of the antimicrobial agent in the otherwise satisfactory growth medium. The diameter of the zone of inhibition is inversely proportional to the MIC.

Alternatively, the concentration of triclosan on the surface of a medical device such as a coated suture may be greater than about 0.01 ppm (wt./wt. coating) or between about 30 ppm to 5,000 ppm (wt./wt. suture). The concentration of triclosan on the surface of package or containment compartment may be between about 5 ppm to 5,000 ppm (wt./wt. package or compartment). For other particular applications, however, higher amounts of antimicrobial agent may be useful and should be considered well within the scope of the present invention.

Method for Making a Packaged Antimicrobial Medical Device

In accordance with various methods of the present invention, a package and containment compartment that are initially substantially free of an antimicrobial agent, i.e., no antimicrobial agent is intended to be present on the package or containment compartment surfaces, may be provided. A medical device, which has an antimicrobial agent disposed thereon, is positioned within the package or containment compartment. Subsequently, the package, the containment compartment if utilized and the medical device are subjected to time, temperature and pressure conditions sufficient to vapor transfer a portion of the antimicrobial agent from the medical device to the package and/or the containment compartment.

The rate of transfer of an antimicrobial agent such as triclosan from the medical device to the package and/or containment compartment is substantially dependent upon the time, temperature and pressure conditions under which the package with the containment compartment and the medical device is processed, stored and handled. For example, FIG. 1 illustrates that triclosan is capable of transferring from a suture to a containment compartment (in a closed vial at atmospheric pressure) when the temperature is maintained at 55 C over a period of time. The conditions to effectively vapor transfer an antimicrobial agent such as triclosan include a closed environment, atmospheric pressure, a temperature of greater than 40 C, for a period of time ranging from 4 to 8 hours. Also included are any combinations of pressure and temperature to render a partial pressure for the antimicrobial agent that is the same as the partial pressure rendered under the conditions described above, in combination with a period of time sufficient to render an effective amount or concentration of the antimicrobial agent on the package and/or containment compartment, i.e., the minimum inhibitory concentration (MIC) or greater. Specifically, it is known to one of ordinary skill that if the pressure is reduced, the temperature may be reduced to effect the same partial pressure. Alternatively, if the pressure is reduced, and the temperature is held constant, the time required to render an effective amount or concentration of the antimicrobial agent on the package and/or containment compartment may be shortened. While a portion of the antimicrobial agent is transferred to the package and/or containment compartment during this process, a second portion is retained on the surface of the medical device.

Accordingly, after the transfer, the medical device and the package and/or the containment compartment contain the antimicrobial agent in an amount effective to substantially inhibit bacterial colonization thereon and thereabout.

Medical devices typically are sterilized to render microorganisms located thereon nonviable. In particular, sterile is understood in the field of art to mean a minimum sterility assurance level of $10^{-6}$. Examples of sterilization processes are described in U.S. Pat. Nos. 3,815,315, 3,068,864, 3,767,362, 5,464,580, 5,128,101 and 5,868,244, each of which is incorporated herein in its entirety. Specifically, absorbable medical devices may be sensitive to radiation and heat. Accordingly, it may be desirable to sterilize such devices using conventional sterilant gases or agents, such as, for example, ethylene oxide gas.

An ethylene oxide sterilization process is described below, since the time, temperature and pressure conditions sufficient to vapor transfer a portion of the antimicrobial agent from the medical device to the package and/or containment compartment, are present in an ethylene oxide sterilization process. However the time, temperature and pressure conditions sufficient to vapor transfer the antimicrobial agent from the medical device to the package and/or containment compartment may be effected alone or in other types of sterilization processes, and are not limited to an ethylene oxide sterilization process or to sterilization processes in general.

As discussed above, absorbable medical devices are sensitive to moisture and are therefore often packaged in hermetically sealed packages, such as sealed foil packages. However, sealed foil packages are also impervious to sterilant gas. In order to compensate for this and utilize foil packages in ethylene oxide gas sterilization processes, processes have been developed using foil packages having gas permeable or pervious vents (e.g., TYVEK polymer). The gas permeable vents are mounted to an open end of the package and allow the passage of air, water vapor and ethylene oxide into the interior of the package. After the sterilization process is complete, the package is sealed adjacent to the vent, and the vent is cut away or otherwise removed, thereby producing a gas impervious hermetically sealed package. Another type of foil package having a vent is a pouch-type package having a vent mounted adjacent to an end of the package, wherein the vent is sealed to one side of the package creating a vented section. After the sterilization process is complete the package is sealed adjacent to the vent, and the package is cut away for the vented section.

The package and containment compartment are substantially free of, and preferably completely free of, antimicrobial agent prior to the transfer of the antimicrobial agent from the medical device to the package and/or the containment compartment. The medical device may first be placed within the containment compartment, if necessary, and then within the package. After the peripheral seal and side seals have been formed in the package, the packaged medical device may be placed into a conventional ethylene oxide sterilization unit. If the package is a foil package, the gas permeable vents described above may be used. Prior to the start of the cycle, the sterilization unit may be heated to an internal temperature of about 25° C. The sterilization unit is maintained about 22 to 37° C. throughout the humidification and sterilization cycles. Next, a vacuum may be drawn on the sterilization unit to achieve a vacuum of approximately 1.8 to 6.0 kPa. In a humidification cycle, steam then may be injected to provide a source of water vapor for the product to be sterilized. The packaged medical devices may be exposed to water vapor in the sterilization unit for a period of time of about 60 to 90 minutes. Times may vary, however, depending upon the medical device being sterilized.

Following this humidification portion of the cycle, the sterilization unit may be pressurized by the introduction of dry inert gas, such as nitrogen gas, to a pressure of between about 42 and 48 kPa. Once the desired pressure is reached, pure ethylene oxide may be introduced into the sterilization unit until the pressure reaches about 95 kPa. The ethylene oxide may be maintained for a period of time effective to sterilize the packaged medical device. For example, the ethylene oxide may be maintained in the sterilization unit for about 360 to about 600 minutes for surgical sutures. The time required to sterilize other medical devices may vary depending upon the type of product and the packaging. The ethylene oxide then may be evacuated from the sterilization unit and the unit may be maintained under vacuum at a pressure of approximately 0.07 kPa for approximately 150 to 300 minutes in order to remove residual moisture and ethylene oxide from the sterilized packaged medical devices. The pressure in the sterilization unit may be returned to atmospheric pressure.

The following stage of the process is a drying cycle. The packaged medical device may be dried by exposure to dry nitrogen and vacuum over a number of cycles sufficient to effectively remove residual moisture and water vapor from the packaged medical device to a preselected level. During these cycles, the packaged medical device may be subjected to a number of pressure increases and decreases, at temperatures greater than room temperature. Specifically, the jacket temperature of the drying chamber may be maintained at a temperature of between approximately 53° C. to 57° C. throughout the drying cycle. Higher temperatures, however, may be employed, such as about 65° C. to 70° C. for sutures, and higher depending upon the medical device being sterilized. A typical drying cycle includes the steps of increasing the pressure with nitrogen to approximately 100 kPa, evacuating the chamber to a pressure of approximately 0.07 kPa over a period of 180 to 240 minutes, reintroducing nitrogen to a pressure of 100 kPa and circulating the nitrogen for approximately 90 minutes, evacuating the chamber to a pressure of approximately 0.01 kPa over a period of approximately 240 to 360 minutes and maintaining a pressure of not more than 0.005 kPa for an additional 4 to 96 hours. At the end of the humidification, sterilization and drying cycles, which takes typically about 24 hours, the vessel is returned to ambient pressure with dry nitrogen gas. Once drying to the preselected moisture level is complete, the packaged medical device may be removed from the drying chamber and stored in a humidity controlled storage area.

Upon completion of the sterilization process, the antimicrobial medical device, the package and/or the containment compartment have thereon an amount of the antimicrobial agent effective to substantially inhibit colonization of bacteria on or adjacent the antimicrobial device, the package and/or the containment compartment.

Example 1

A series of USP standard size 5-0 coated polyglactin 910 sutures were coated with a 2% triclosan coating composition so that each suture contained about a total of 23.2 μg triclosan before sterilization. The coated sutures each were placed in a package as described herein above including a containment component, i.e., a tray, for holding the suture and a paper component for covering the suture in the tray. The suture in the containment component and packaging were sterilized as described herein above. After sterilization, it was determined that that suture contained about 5.5 μg triclosan, the tray about 0.2 µg triclosan, the paper component about 2.3 µg triclosan, and the package heat seal coating about 1.5 µg triclosan. Triclosan not recovered after sterilization was about 13.7 µg triclosan. FIG. 1 indicates triclosan transfer from the antimicrobial suture to the tray of the package as a function of time at 55° C.

After sterilization, the paper component and tray of the sterilized package were tested for antimicrobial properties utilizing a zone of inhibition test as indicated herein below. Zone of inhibition testing is a conventional method for estimating the inhibitory effects of antimicrobial substances against specific bacterial strains of interest. Zone of inhibition assays are useful for testing diffusible agents. As the agent diffuses away from the disk, the concentration decreases logarithmically. The sensitivity of the organism to the agent is judged by the appearance and size of a zone where no growth occurs, i.e., the zone of inhibition.

A comparative example of a package that contained a conventional commercially available suture, i.e., not having triclosan applied thereto, also was prepared and tested for antimicrobial properties.

Figure 2:
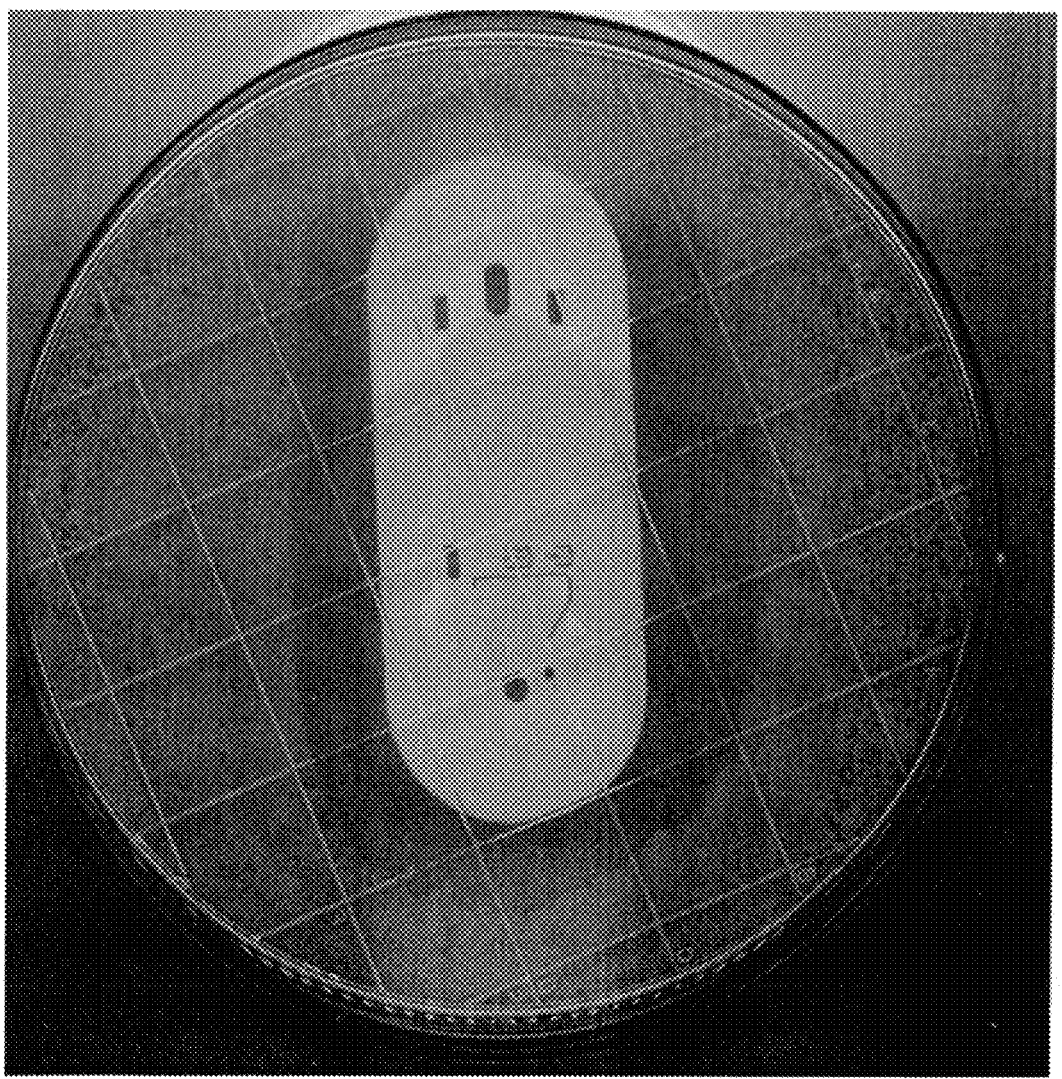
FIG. 2 is a photographic representation of a containment compartment on a TSA plate challenged *Staphylococcus aureus*.

FIG. 2 is a photographic representation of the zone of inhibition with respect to a tray of the antimicrobial package on a TSA plate challenged with *Staphylococcus aureus*.

The results of the zone of inhibition assays for the paper component and tray are listed in Table 1. The zones were measured for both treated and untreated tray and paper component. As shown in Table 1, zones of inhibition were present for all treated components against both *Staphylococcus aureus* and *Staphylococcus epidermidis*. The untreated components exhibited no zones of inhibition.

TABLE 1

Zone of Inhibition Assay for Package Components

| Treated Package Component | Zone size | Untreated Package Component | Zone size |
|---|---|---|---|
| *Staphylococcus epidermidis* | | | |
| Tray | 18 mm | Tray | 0 |
| Paper | 13 mm | Paper | 0 |
| *Staphylococcus aureus* | | | |
| Tray | 12 mm | Tray | 0 |
| Paper | 13 mm | Paper | 0 |

Example 2

This example is a 24-hour aqueous immersion assay. The purpose of this assay was to determine the effect of aqueous exposure on the antimicrobial properties of suture material for a range of suture diameters. Sterile sutures in USP sizes 2-0, 3-0, 4-0, and 5-0, with and without a 1% triclosan coating applied thereto, were aseptically cut into 5-cm pieces. One half of the cut pieces were stored in a sterile Petri dish and kept under a dry nitrogen atmosphere for 24 hours (dry suture). One half of the cut pieces were aseptically transferred to sterile 0.85% saline and incubated at 37° C. for 24 hours (wet sutures).

The dry and wet sutures were then aseptically placed in individual sterile Petri dishes and challenged with 100 microliters of inoculum containing $10^5$ colony-forming units (CFU) of *Staphylococcus aureus* or *Staphylococcus epidermidis*. Ten replicates of each suture size were used for each organism and for both the dry and wet sample groups. TSA was poured into each dish and allowed to solidify. The plates were incubated at 37° C. for 48 hours. After incubation, the plates were examined under a darkfield colony counter and the zones of inhibition were measured.

Figure 3:
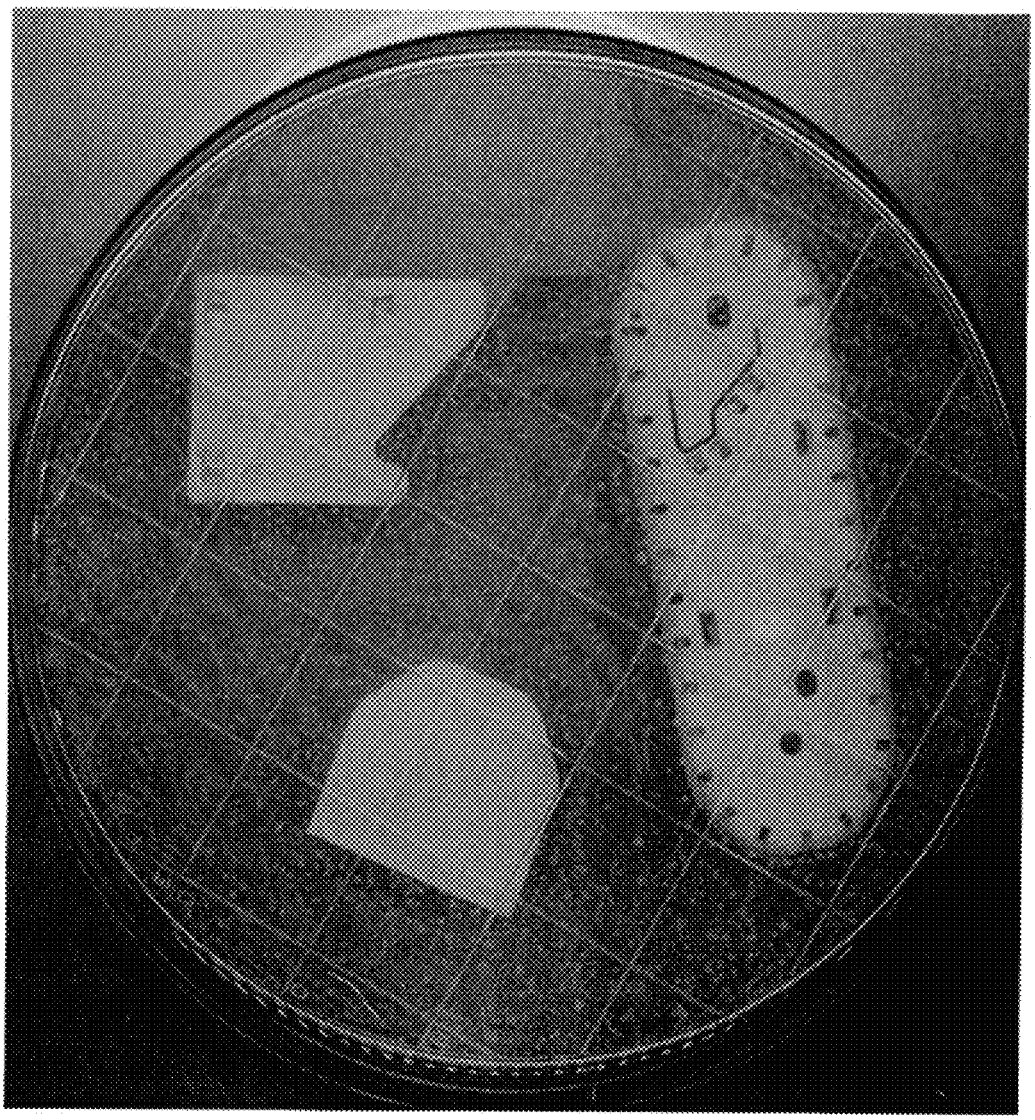
FIG. 3 is a photographic representation of a suture on a TSA plate challenged *Staphylococcus epidermidis*.

The results of the zone of inhibition assays are listed in Table 2. Zones of inhibition were present for all sizes of coated polyglactin 910 suture having triclosan applied thereto. Both the dry and wet samples exhibited significant zones of inhibition. The coated polyglactin 910 suture controls had no zones of inhibition. A typical zone of inhibition is depicted in FIG. 3.

TABLE 2

24 Hour Aqueous Immersion Assay: Zone of Inhibition Diameter

| | Zone Diameter Average (mm) | | | |
|---|---|---|---|---|
| Suture | S aureus | | S epidermidis | |
| Material | Dry | Wet | Dry | Wet |
| Size 2-0 | | | | |
| +Triclosan | 10 | 9 | 10 | 9 |
| Control | 0 | 0 | 0 | 0 |
| Size 3-0 | | | | |
| +Triclosan | 10 | 10 | 10 | 8 |
| Control | 0 | 0 | 0 | 0 |
| Size 4-0 | | | | |
| +Triclosan | 10 | 3 | 10 | 2 |
| Control | 0 | 0 | 0 | 0 |
| Size 5-0 | | | | |
| +Triclosan | 10 | 3 | 10 | 2 |
| Control | 0 | 0 | 0 | 0 |

All suture samples were from different lots. Average zone diameter is based on triplicate plates.

As shown in FIG. 3, areas of inhibited bacterial growth were observed around coated polyglactin 910 suture containing triclosan, while the control suture without triclosan had confluent bacterial growth. The response was similar for *Staphylococcus epidermidis* (shown), *Staphylococcus aureus*, MRSA, and MRSE, and was consistent for a variety of suture sizes.

Example 4

This example is directed to a 7-day aqueous immersion assay. The purpose of this assay was to determine if the antimicrobial effect of triclosan treatment would endure for 7 days in a buffered aqueous environment.

Sterile USP size 2-0 coated polyglactin 910 suture coated with a 1%, 2%, and 3% triclosan coating solution, respectively, and ethylene oxide sterilized USP size 2-0 coated polyglactin suture were aseptically cut into 5-cm pieces. Samples were tested on each of 7 days in triplicate.

On day 1, 3 pieces of each suture material were placed into individual sterile Petri dishes and inoculated with 0.1 mL of challenge organism containing approximately $10^4$ CFU. TSA was poured into each dish and allowed to solidify. All remaining pieces of suture material were placed into 100 mL of sterile phosphate buffered 0.85% saline (PBS). Every 24 hours for the next 6 days, 3 pieces of each suture material were removed from the PBS, inoculated, and pour plated in tryptic/soy/agar (TSA). All plates were incubated at 37° C. for 48 hours and the plates examined for the presence or absence of a zone of inhibition.

The results for the 7-day assay are presented in Table 4. The coated polyglactin 910 suture with triclosan produced zones of inhibition after every challenge. The control coated polyglactin 910 suture without triclosan produced no growth inhibition.

TABLE 4

7-Day Aqueous Immersion Assay: Zone of Inhibition Diameter

| Triclosan coating | Zone Diameter Average (mm) Day | | | | | | |
|---|---|---|---|---|---|---|---|
| | 1 | 2 | 3 | 4 | 5 | 6 | 7 |
| 1% | 20 | 18 | 20 | 20 | 19 | 21 | 20 |
| 2% | 24 | 20 | 22 | 21 | 24 | 24 | 23 |
| 3% | 27 | 25 | 15 | 25 | 27 | 30 | 27 |
| Control (0%) | 0 | 0 | 0 | 0 | 0 | 0 | 0 |

All suture samples were from different lots. Average diameter is based on triplicate plates.

This example is a demonstration of the efficacy of the antimicrobial suture where samples of the antimicrobial suture and a conventional suture were each separately exposed by immersion in aqueous buffer as a model of physiological conditions for up to seven days. On each day, samples of both the conventional and the antimicrobial suture of the invention were removed and placed on tryptic/soy/agar (TSA) plates that had been inoculated with a $10^4$ colony forming unit (CFU) Staphylococcus challenge. As is shown in Table 4, the antimicrobial suture of the invention developed a zone of inhibition around it on the plate, even after seven days of immersion, providing evidence that the concentration of the antimicrobial agent on and around the antimicrobial suture of the invention was still above the MIC, while the conventional sutures, treated similarly, developed no zone of inhibition, i.e. the microorganisms freely grew on and around the conventional suture.

Example 6

This example relates to scanning electron microscopy. Scanning electron microscope (SEM) images were prepared using sutures that had been exposed to MRSE in broth culture. Single 6-inch strands of USP size 2-0 coated polyglactin 910 suture coated with 0.5% triclosan coating solution were placed in separate tubes containing 30 mL of sterile TSB and inoculated with 0.1 mL of a 24-hour culture of the challenge organism in TSB. Single 6-inch strands of USP size 2-0 Polysorb® (braided lactomer 9-1) suture, available from United States Surgical Corporation, and which did not contain triclosan, were also prepared in the same fashion. The tubes were incubated for 24 hours at 37° C. After incubation, the sutures were prepared for SEM as follows.

Each strand of the suture was removed from the broth and rinsed by vortexing in 100 mL of sterile saline for 10 seconds. The rinsed strands were fixed in 10% buffered formalin for 5 minutes. The fixed strands were dehydrated in ethanol using sequential 5-minute exposures of 50%, 70%, 85%, 95%, and 100% ethanol. A final dehydration was performed using a 5-minute exposure in hexamethylenedisilazane. The samples were air dried prior to SEM. The SEM used for imaging the bacteria was a JEOL (Japan Electronics and Optics Laboratory) JSM-5900LV scanning electron microscope.

Figure 4:
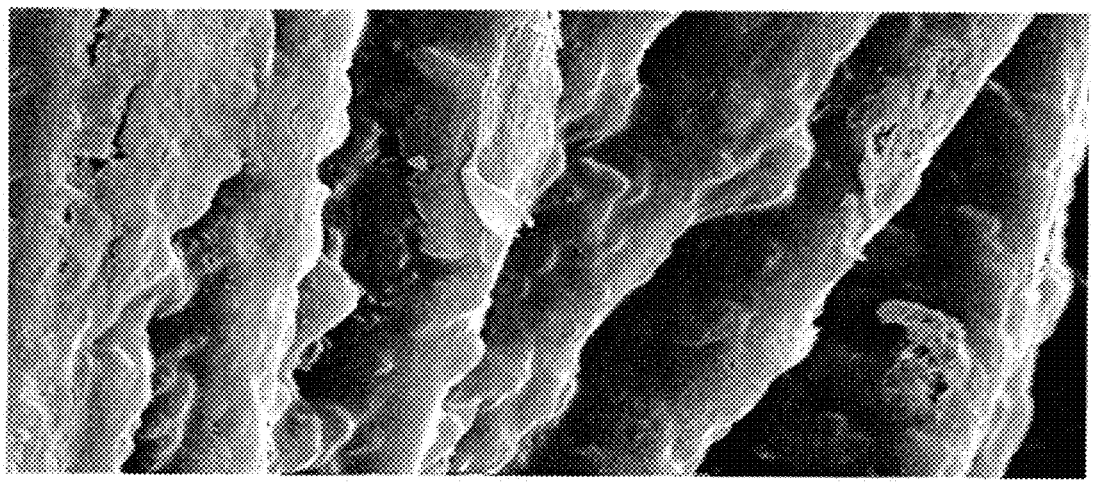
FIG. 4 is a scanning electron microscope ("SEM") image of suture strands coated with an antimicrobial composition and exposed to methicillin-resistant *Staphylococcus epidermidis*.
Figure 5:
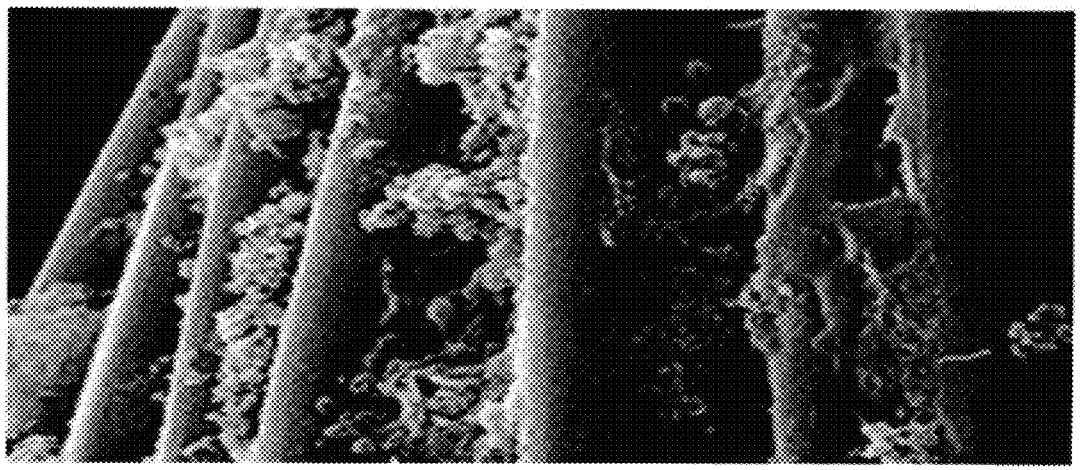
FIG. 5 is a scanning electron microscope ("SEM") image of suture strands, which are not coated with an antimicrobial composition, exposed to methicillin-resistant *Staphylococcus epidermidis*.

FIGS. 4 and 5 illustrate the differences between the triclosan-treated suture (a) and the untreated suture (b). The triclosan-treated suture had very few bacteria associated with it anywhere on the surface, while the untreated suture was uniformly and heavily coated with bacteria.

The data presented above indicate that coated polyglactin 910 suture with triclosan exhibits antimicrobial activity in vitro against Staphylococcus aureus and Staphylococcus epidermidis compared to untreated controls. This activity is evident on a range of suture diameters. The antimicrobial activity endures despite extended exposure to a buffered aqueous environment. Methicillin-resistant strains of Staphylococcus aureus and Staphylococcus epidermidis were inhibited after 24 hours of aqueous extraction by polyglactin 910 with triclosan at low triclosan concentrations. Low levels of triclosan on the suture are sufficient to greatly reduce colonization of the suture compared to controls as illustrated by scanning electron microscopy. These data support the conclusion that coated polyglactin 910 suture with triclosan provides an antimicrobial effect sufficient to prevent in vitro colonization of the suture by Staphylococcus aureus and Staphylococcus epidermidis.

Moreover, coated medical devices may be stable for extended periods of time. During storage, coated devices may maintain a sufficient amount of triclosan to exhibit desired antimicrobial effects. Standard accelerated aging tests may be used to estimate antimicrobial properties after exposure to typical storage conditions.

Upon exposure to accelerated aging tests, triclosan coated sutures exhibited zones of inhibition against Staphylococcus aureus and Staphylococcus epidermidis. In particular, triclosan coated sutures were exposed to 50° C. for 157 days. Table 6 indicates triclosan loss from various USP size 2-0 coated dyed polyglactin 910 sutures with varying levels of triclosan upon exposure of the sutures to 50° C. for 157 days. The exposure took place after the sutures had been ethylene oxide sterilized and placed in a hot room for three days. Table 7 exhibits antimicrobial properties of those sutures after such exposure. As indicated in Table 7, zones of inhibition were exhibited against both Staphylococcus aureus and Staphylococcus epidermidis after exposure. Although no zones of inhibition were exhibited against Streptococcus agalacticae under these testing conditions, higher concentrations of triclosan are known to inhibit growth of Streptococcus agalacticae. It is important to note that standard accelerated aging tests do not employ true hospital storage conditions, and thus, typically demonstrate worst-case scenarios. As such, the stability of triclosan coated sutures is believed to be significantly longer under normal shelf-storage conditions.

TABLE 6

Triclosan Loss at 50° C. for 2-0 Dyed Vicryl Suture after Ethylene Oxide Sterilization and 3 Days in Hot Room

| 1% Solution | | 2% Solution | | 3% Solution | |
|---|---|---|---|---|---|
| at 50° C. Days | Irgacare ppm | at 50° C. Days | Irgacare ppm | at 50° C. Days | Irgacare ppm |
| 0 | 200 | 0 | 295 | 0 | 333 |
| 3 | 127 | 3 | 216 | 3 | 266 |
| 3 | 132 | 3 | 235 | 3 | 291 |
| 3 | 156 | 3 | 230 | 3 | 291 |
| 11 | 94 | 11 | 163 | 11 | 227 |
| 11 | 91 | 11 | 163 | 11 | 213 |
| 18 | 89 | 18 | 140 | 18 | 189 |
| 32 | 69 | 32 | 120 | 32 | 155 |
| 58 | 58 | 58 | 108 | 58 | 164 |
| 157 | 59 | 157 | 118 | 157 | 130 |
| 157 | 39 | 157 | 79 | 157 | 101 |

TABLE 7

Zones of Inhibition for 2-0 Dyed Vicryl Suture after Exposure to 50° C. for 157 Days

| Triclosan Coating Conc. (%) | Triclosan on Suture (ppm) | Storage Conditions/ Sterilization Cycle | Zone of Inhibition (Yes/No) | | | | | |
|---|---|---|---|---|---|---|---|---|
| | | | S. aureus | | Strep agalacticae | | S. epidermidis | |
| | | | 24 hr. | 48 hr. | 24 hr. | 48 hr. | 24 hr. | 48 hr. |
| 1.0 | 39 | 50 C. for 157 days/N cycle | No Yes | No No | No No | No No | No Yes | No Yes |
| 2.0 | 79 | 50 C. for 157 days/N cycle | Yes | Yes | No | No | Yes | Yes |
| 3.0 | 101 | 50 C. for 157 days/N cycle | Yes | Yes | No | No | Yes | Yes |
| 1.0 | 59 | 50 C. for 157 days/N cycle | Yes | No | No | No | Yes | Yes |
| 2.0 | 118 | 50 C. for 157 days/N cycle | Yes | Yes | No | No | Yes | Yes |
| 3.0 | 130 | 50 C. for 157 days/N cycle | Yes | Yes | No | No | Yes | Yes |

What is claimed:

1. A method of making a packaged antimicrobial suture comprising the steps of:
   providing a containment compartment that is substantially free of an antimicrobial agent;
   positioning a suture within the containment compartment, said suture comprising one or more surfaces having an antimicrobial agent disposed thereon, said antimicrobial agent being selected from the group consisting of halogenated hydroxyl ethers, acyloxydiphenyl ethers, and combinations thereof;
   placing the containment compartment having the suture in an outer package; and
   subjecting the outer package, the containment compartment and the suture to time, temperature and pressure conditions sufficient to vapor transfer an effective amount of the antimicrobial agent from the suture to an inner surface of the containment compartment, while retaining an effective amount of said antimicrobial agent on the suture, thereby substantially inhibiting bacterial colonization on the suture and the containment compartment,
   wherein said step of subjecting the outer package, the containment compartment and the suture to conditions sufficient to vapor transfer an effective amount of the antimicrobial agent from the suture to an inner surface of the containment compartment, while retaining an effective amount of said antimicrobial agent on the suture includes adjusting the pressure to not more than 0.005 kPa at a temperature greater than room temperature.

2. The method for making a packaged antimicrobial suture according to claim 1, wherein said step of subjecting the outer package, the containment compartment and the suture to conditions sufficient to vapor transfer an effective amount of the antimicrobial agent from the suture to an inner surface of the containment compartment, while retaining an effective amount of said antimicrobial agent on the suture includes an ethylene oxide sterilization process.

3. The method for making a packaged antimicrobial suture according to claim 1, wherein the step of subjecting the outer package, the containment compartment and the suture to conditions sufficient to vapor transfer an effective amount of the antimicrobial agent from the suture to an inner surface of the containment compartment, while retaining an effective amount of said antimicrobial agent on the suture further comprises the steps of:
   placing the outer package having the containment compartment and the suture therein in a sterilization unit;
   heating the sterilization unit to a first temperature;
   adjusting the pressure in the sterilization unit to a first pressure value;
   injecting steam into the sterilization unit to expose the outer package, the containment compartment and the suture to water vapor for a first period of time;
   adjusting the pressure within the sterilization unit to a second pressure value;
   introducing a chemical sterilization agent into the sterilization unit;
   maintaining the chemical sterilization agent in the sterilization unit for a second period of time to render a sufficient amount of microorganisms within the package nonviable;
   removing residual moisture and chemical sterilization agent from the suture; and
   drying the packaged antimicrobial suture to a desired moisture level.

4. The method for making a packaged antimicrobial suture according to claim 3, wherein the step of introducing a chemical sterilization agent comprises introducing ethylene oxide gas into the sterilization unit.

5. A method of making a packaged medical device comprising the steps of:
   providing a package comprising an inner surface that is substantially free of an antimicrobial agent;
   positioning a medical device within the package, said medical device comprising one or more surfaces having an antimicrobial agent disposed thereon, said antimicrobial agent being selected from the group consisting of halogenated hydroxyl ethers, acyloxydiphenyl ethers, and combinations thereof; and
   subjecting the package and the medical device to time, temperature and pressure conditions sufficient to vapor transfer an effective amount of the antimicrobial agent from the medical device to the inner surface of the package, while retaining an effective amount of said antimicrobial agent on the medical device, thereby substantially inhibiting bacterial colonization on the medical device and the inner surface of the package, wherein said step of subjecting the outer package, the containment compartment and the suture to conditions sufficient to vapor transfer an effective amount of the antimicrobial agent from the suture to an inner surface of the containment compartment, while retaining an effective amount of said antimicrobial agent on the suture includes adjusting the pressure to not more than 0.005 kPa at a temperature greater than room temperature.

6. The method of claim 1, wherein the suture comprising one or more surfaces having an antimicrobial agent disposed thereon further comprises at least one active agent selected from the group consisting of a biocide, a disinfectant, an antiseptic, an antibiotic, an antimicrobial peptide, a lytic bacteriophage, a surfactant; an adhesion blocker; an oligonucleotide, an efflux pump inhibitors; a photosensitive dye, an immune modulator and a chelator.

7. The method of claim 5, wherein the medical device comprising one or more surfaces having an antimicrobial agent disposed thereon further comprises at least one active agent selected from the group consisting of a biocide, a disinfectant, an antiseptic, an antibiotic, an antimicrobial peptide, a lytic bacteriophage, a surfactant; an adhesion blocker; an oligonucleotide, an efflux pump inhibitors; a photosensitive dye, an immune modulator and a chelator.

8. The method according to claim 5, wherein said step of subjecting the outer package, the containment compartment and the suture to conditions sufficient to vapor transfer an effective amount of the antimicrobial agent from the suture to an inner surface of the containment compartment, while retaining an effective amount of said antimicrobial agent on the suture includes an ethylene oxide sterilization process.

9. The method according to claim 8, wherein the package is subjected to a pressure of less than about 1.0 kPa.

* * * * *